(12) United States Patent
Schmidt et al.

(10) Patent No.: US 7,282,246 B2
(45) Date of Patent: Oct. 16, 2007

(54) FLUORINATED XANTHENES AND USE THEREOF IN LIQUID-CRYSTAL MIXTURES

(75) Inventors: Wolfgang Schmidt, Dreieich (DE); Barbara Hornung, Hasselroth (DE); Rainer Wingen, Hofheim (DE)

(73) Assignee: Merck Patent GmbH, Darmstadt (DE)

( * ) Notice: Subject to any disclaimer, the term of this patent is extended or adjusted under 35 U.S.C. 154(b) by 67 days.

(21) Appl. No.: 11/098,084

(22) Filed: Apr. 4, 2005

(65) Prior Publication Data
US 2005/0274929 A1 Dec. 15, 2005

(51) Int. Cl.
*C09K 19/34* (2006.01)
*C09K 19/32* (2006.01)
*C07D 311/82* (2006.01)
*C07C 23/28* (2006.01)

(52) U.S. Cl. ............ 428/1.1; 252/299.61; 252/299.62; 549/223; 549/385; 570/142; 570/183; 570/187

(58) Field of Classification Search ................. 428/1.1; 252/299.61, 299.62; 549/223, 385; 570/142, 570/183, 187
See application file for complete search history.

(56) References Cited

U.S. PATENT DOCUMENTS
6,558,758 B1 5/2003 Yanai et al.

FOREIGN PATENT DOCUMENTS
DE 100 50 071 A1 6/2001

OTHER PUBLICATIONS
CAPLUS 1975: 479029.*
CAPLUS 1981: 47140.*

Ichinose et al, High Optical Anisotropy and Small Rotational Viscosity LC Mixture for Field-Sequential Color TN-LCD's, Abstract LCT4-3, 2000, pp. 77 to 80; Seventh International Display Workshop, Nov. 29-Dec. 1, 2000, Kobe, Japan.

* cited by examiner

Primary Examiner—Shean C Wu
(74) Attorney, Agent, or Firm—Frommer Lawrence & Haug, LLP

(57) ABSTRACT

Concerning the compound of the formula (I)

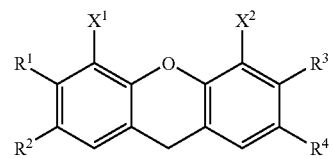

(I)

$R^1$, $R^3$ are each independently, for example, H
$R^2$, $R^4$ are each independently, for example, H
$X^1$, $X^2$ are each independently H or F
$M^1$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond
$A^1$ is, for example, 1,4-phenylene, and
$R^5$ has the same possible definitions as specified for $R^2$ and $R^4$, with the exception of —$M^1$-$A^1$-$R^5$, but independently of the particular definitions of $R^2$ and $R^4$
with the following provisos:
1) at least one of $X^1$, $X^2$ has to be F
2) $R^1$, $R^2$, $R^3$ and $R^4$ must not at the same time be H
3) at most two of $R^1$, $R^2$, $R^3$ and $R^4$ may be c).

19 Claims, 1 Drawing Sheet

FLUORINATED XANTHENES AND USE THEREOF IN LIQUID-CRYSTAL MIXTURES

An ever-increasing number of applications of LCDs, for example for use in automobiles, in which a temperature range of from −40° C. to 100° C. can quite possibly exist, but also portable units such as cellphones and notebook PCs, requires liquid-crystal mixtures which have firstly a very wide working temperature range and secondly a very low threshold voltage.

There is therefore a continuing demand for novel, suitable liquid-crystal mixtures and mixture components. As described in Ichinose et al. (IDW'00, Abstr. LCT4-3) or in DE-A 10050071, materials are being sought in which there is coexistence of high optical anisotropy (Δn) and low rotational viscosity, although other parameters such as high absolute values of dielectric anisotropy (Δε) are likewise preferentially required, in addition to further parameters relevant to the application.

Since the manufacturers of liquid-crystal displays have an interest in constantly improved liquid-crystal mixtures, there is still a need for further components of liquid-crystal mixtures, with which individual parameters relevant to the application, for example the dielectric anisotropy Δε, may be optimized.

It is therefore an object of the present invention to provide novel components for use in nematic or cholesteric or chiral-smectic liquid-crystal mixtures which have high absolute values of dielectric anisotropy combined with a favorable ratio of viscosity to clearing point. In addition, the compounds should to a high degree preferably be light- and UV-stable, and also thermally stable. In addition, they should preferably be suitable for realizing a high voltage holding ratio (VHR). In addition, they should preferably have good synthetic accessibility and therefore potentially be inexpensive.

According to the invention, the objects are achieved by compounds of the formula (I)

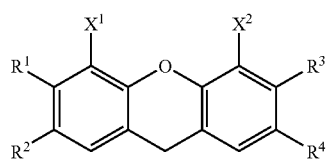

(I)

in which
$R^1$, $R^3$ are each independently
a) H
b) one of $R^1$ and $R^3$ is —$M^1$—$A^1$—$R^5$
c) a straight-chain or branched alkyl radical having from 1 to 16 carbon atoms or a straight-chain or branched alkenyl radical having from 2 to 16 carbon atoms, in which
   c1) one or more nonadjacent and nonterminal $CH_2$ groups may be replaced by —O—, —C(=O)O—, —O—C(=O)—, —O—C(=O)—O—, —C(=O)— or —Si($CH_3$)$_2$— and/or
   c2) one $CH_2$ group may be replaced by —C≡C—, cyclopropane-1,2-diyl, cyclobutane-1,3-diyl, cyclohexane-1,4-diyl or phenylene-1,4-diyl and/or
   c3) one or more hydrogen atoms may be replaced by F and/or Cl
d) F, Cl, $CF_3$, $OCF_3$, $OCF_2H$
$R^2$, $R^4$ are each independently
a) H
b) one of $R^2$ and $R^4$ is —$M^1$—$A^1$—$R^5$
c) a straight-chain or branched alkyl radical having from 1 to 16 carbon atoms or a straight-chain or branched alkenyl radical having from 2 to 16 carbon atoms, in which
   c1) one or more nonadjacent and nonterminal $CH_2$ groups may be replaced by —O—, —C(=O)O—, —O—C(=O)—, —O—C(=O)—O—, —C(=O)— or —Si($CH_3$)$_2$— and/or
   c2) one $CH_2$ group may be replaced by —C≡C—, cyclopropane-1,2-diyl, cyclobutane-1,3-diyl, cyclohexane-1,4-diyl or phenylene-1,4-diyl and/or
   c3) one or more hydrogen atoms may be replaced by F and/or Cl
$X^1$, $X^2$ are each independently H or F
$M^1$ is —CO—O—, —O—CO—, —$CH_2$—O—, —O—$CH_2$—, —$CF_2$—O—, —O—$CF_2$—, —CH=CH—, —CF=CF—, —C≡C—, —$CH_2$—$CH_2$—CO—O—, —O—CO—$CH_2$—$CH_2$—, —$CH_2$—$CH_2$—, —$CF_2$—$CF_2$—, —($CH_2$)$_4$—, —OC(=O)CF=CF— or a single bond
$A^1$ is 1,4-phenylene in which one or two hydrogen atoms may be replaced by F, Cl, CN and/or $OCF_3$ or three hydrogen atoms may be replaced by fluorine, 1,4-cyclohexylene in which one or two hydrogen atoms may be replaced by $CH_3$ and/or F, 1-cyclohexene-1,4-diyl in which one hydrogen atom may be replaced by $CH_3$ or F, pyridine-2,5-diyl, pyrimidine-2,5-diyl or 1,3-dioxane-2,5-diyl and
$R^5$ has the same possible definitions as specified for $R^2$ and $R^4$, with the exception of —$M^1$—$A^1$—$R^5$, but independently of the particular definitions of $R^2$ and $R^4$ with the following provisos:
1) at least one of $X^1$, $X^2$ has to be F
2) $R^1$, $R^2$, $R^3$ and $R^4$ must not at the same time be H
3) at most two of $R^1$, $R^2$, $R^3$ and $R^4$ may be c).

Preference is given to compounds of the formulae (Ia) to (Id):

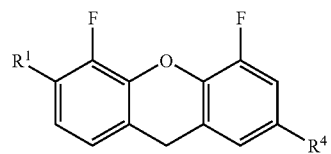

(Ia)

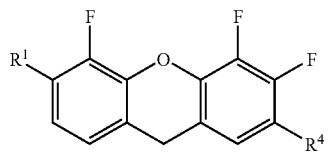

(Ib)

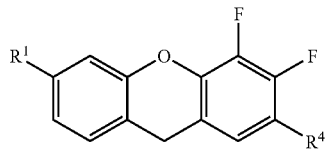

(Ic)

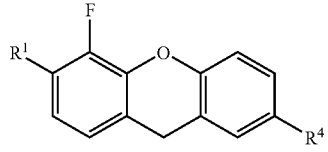

(Id)

Particular preference, especially for use in nematic mixtures, is given to compound of the formulae (Ia), (Ib), (Ic) and (Id), in which $R^1$ and $R^4$ are each independently an alkyl or alkyloxy radical having from 1 to 6 carbon atoms or an alkenyl or alkenyloxy radical having from 2 to 5 carbon atoms or the $R^5$—$A^1$—$M^1$—moiety, with the proviso that $R^1$ and $R^4$ must not be at the same time $R^5$—$A^1$—$M^1$—.

For use in smectic liquid-crystal mixtures, particular preference is given to compounds of the formulae (Ia), (Ib), (Ic) and (Id), in which one of the $R^1$ and $R^4$ radicals is —$M^1$—$A^1$—$R^5$; very particular preference is given to $A^1$ in these compounds being pyrimidine-2,5-diyl.

The provision of compounds of the formula (I) in a quite general sense considerably broadens the range of liquid-crystalline substances which are suitable for producing liquid-crystalline mixtures from different performance aspects.

In this context, the compounds of the formula (I) have a broad field of application. Depending on the selection of the substituents, they may be added to other classes of compound, in order, for example, to influence the dielectric and/or optical anisotropy of such a dielectric. They may also serve to optimize its threshold voltage and/or its viscosity. The compounds may also serve to increase the mesophase range or to adjust individual mesophases to parameters relevant to the application.

The compounds of the formula (I) are particularly suitable, even in small amounts in the mixture, for influencing the dielectric anisotropy ($\Delta\epsilon$) of liquid-crystal mixtures, especially to higher negative absolute values of the dielectric anisotropy.

The compounds of the formula (I) are particularly suitable, even in small amounts in the mixture, for reducing the response time of ferroelectric liquid-crystal mixtures. The compounds of the formula (I) are likewise particularly suitable for adjusting the broadness of the $S_C$ or N phase to application requirements.

The present invention thus provides, in addition to the compounds of the formula (I), the use of these compounds as components of liquid-crystalline mixtures and liquid-crystal mixtures comprising one or more compounds of the formula (I).

The compounds of the formula (I) may be used in various liquid-crystal mixtures, for example (chiral)-smectic, nematic or cholesteric liquid-crystal mixtures. In the case of nematic mixtures, they are particularly suitable for active matrix displays (AM-LCD) (see, for example, C. Prince, Seminar Lecture Notes, Volume I, p. M-3/3-M-22, SID International Symposium 1997, B. B: Bahadur, Liquid Crystal Applications and Uses, Vol. 1, p. 410, World Scientific Publishing, 1990, E. Lüder, Recent Progress of AMLCD's, Proceedings of the 15$^{th}$ International Display Research Conference, 1995, p. 9-12) and in-plane-switching displays (IPS-LCD), and, in the case of smectic liquid-crystal mixtures, for smectic (ferroelectric or antiferroelectric) displays. Further display possibilities are the ECB and VA display mode in the case of nematic and cholesteric LC mixtures.

Further components of liquid-crystal mixtures which comprise inventive compounds of the formula (I) are preferably selected from the known compounds having smectic and/or nematic and/or cholesteric phases. Mixture components suitable in this context are listed in particular in WO 00/36054, DE-A-19 531 165 and EP-A-0 893 424, which are explicitly incorporated herein by way of reference.

The present invention therefore also provides liquid-crystal mixtures, which comprise at least one compound of the formula (I), preferably in an amount of from 1 to 40% by weight, based on the liquid-crystal mixture. The mixtures preferably comprise at least 3 further components having (chiral)-smectic and/or nematic and/or cholesteric phases in addition to compounds of the formula (I). The invention additionally provides electrooptical display elements (liquid-crystal displays) which comprise the inventive mixtures.

Preference is given to displays which comprise the inventive nematic or smectic (ferroelectric or antiferroelectric) mixtures in combination with active matrix elements.

The inventive displays are typically constructed in such a way that one liquid-crystal layer is enclosed on both sides by layers which are typically, in this sequence starting from the LC layer, at least one alignment layer, electrodes and a boundary layer (for example of glass). In addition, they may comprise spacers, adhesive frames, polarizers and thin color filter layers for color displays. Further possible components are antireflection, passivation, compensation and barrier layers, and also electrically nonlinear elements such as thin-film transistors (TFT) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

Examples of possible synthetic routes to compounds of the formula (I) are specified in schemes 1 and 2, although other processes are feasible and possible.

The reactants are known from the literature and/or are commercially available:

(E1): 2-Bromo-6-fluorophenol [2040-89-3]; (E2): 1,2,3-trifluorobenzene [1489-53-8];

(E3): 1,2-difluorobenzene [367-11-3]; (E4): 2-hydroxy-5-methylbenzaldehyde [613-84-3]

The reaction conditions of the individual stages are:

a) MeOH, (Ph)$_3$P, DEAD according to *Synthesis* 1981, 1 b) n-BuLi, Et$_2$O, −75° C. according to *J. Chem. Soc. Perkin Trans. I*, 1995, 2729 c) 1. LiCOR, THF, −75° C. 2. $R^3$Br or $R^1$Br according to Recl. Trav. Chim. Pay-Bas 1994, 113, 52 d) 1. LDA, THF, −75° C. 2. DMF 3. H$_3$O$^+$ according to DE-100 22 661 e) according to *Organikum*, 15$^{th}$ edition 1977, Ch. 7.3.6 f) TosCl, pyridine according to *Organikum*, 15$^{th}$ edition 1977, p. 684 g) LiAlH$_4$ according to *J. Am. Chem. Soc.* 1951, 73, 2872 h) BBr$_3$, DCM according to *Synthesis* 1983, 249 i) K$_2$CO$_3$, DMF, 100° C. according to *New. J Chem* 2001, 25, 385 j) 1. Metalation according to *J. Chem. Soc. Perkin Trans I*, 1995, 2729.

2. Reaction with $R^1$Br according to *Tetrahedron Letters* 1996, 37, 6551.

| | |
|---|---|
| n-BuLi | n-Butyllithium |
| DCC | Dicyclohexylcarbodiimide |
| DCM | Dichloromethane |
| DEAD | Diethyl azodicarboxylate |
| Diglyme | Diethylene glycol dimethyl ether |
| DMAP | 4-(Dimethylamino)pyridine |
| DME | Dimethoxyethane |
| DMF | N,N-Dimethylformamide |
| KOtBu | Potassium tert-butoxide |
| LDA | Lithium diisopropylamide |
| LiCOR | Lithium organyl + potassium tert-butoxide |
| LiTMP | Lithium 2,2,6,6-tetramethylpiperidide |
| MEK | Methyl ethyl ketone (2-butanone) |
| MTBE | tert-Butyl methyl ether |
| TosCl | 4-Toluenesulfonyl chloride |

Scheme 1
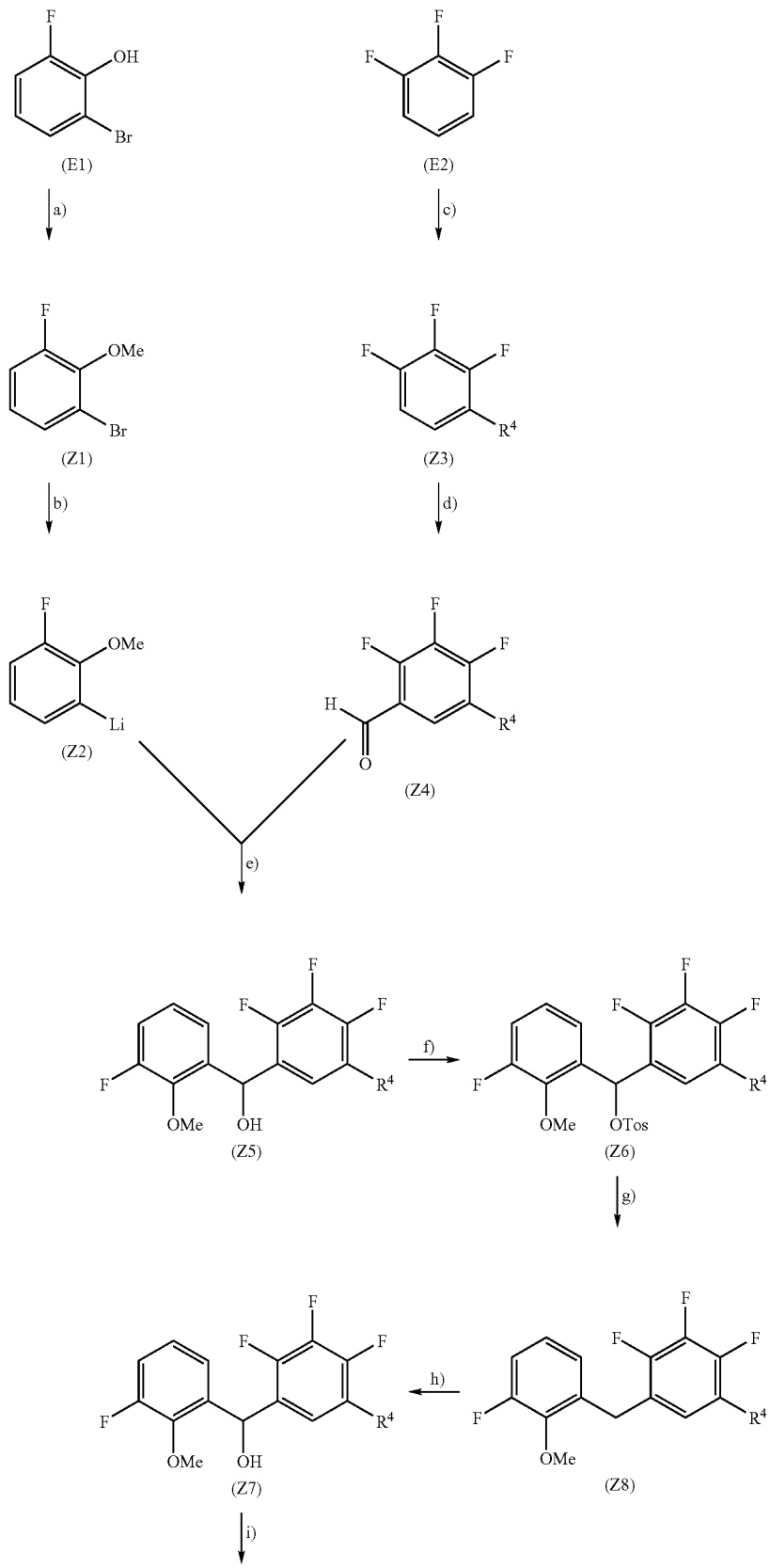

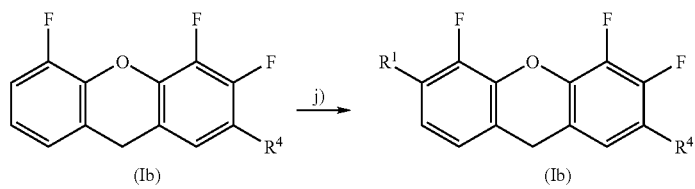
(Ib) → (Ib)  
($R^1$ = H)
Scheme 2
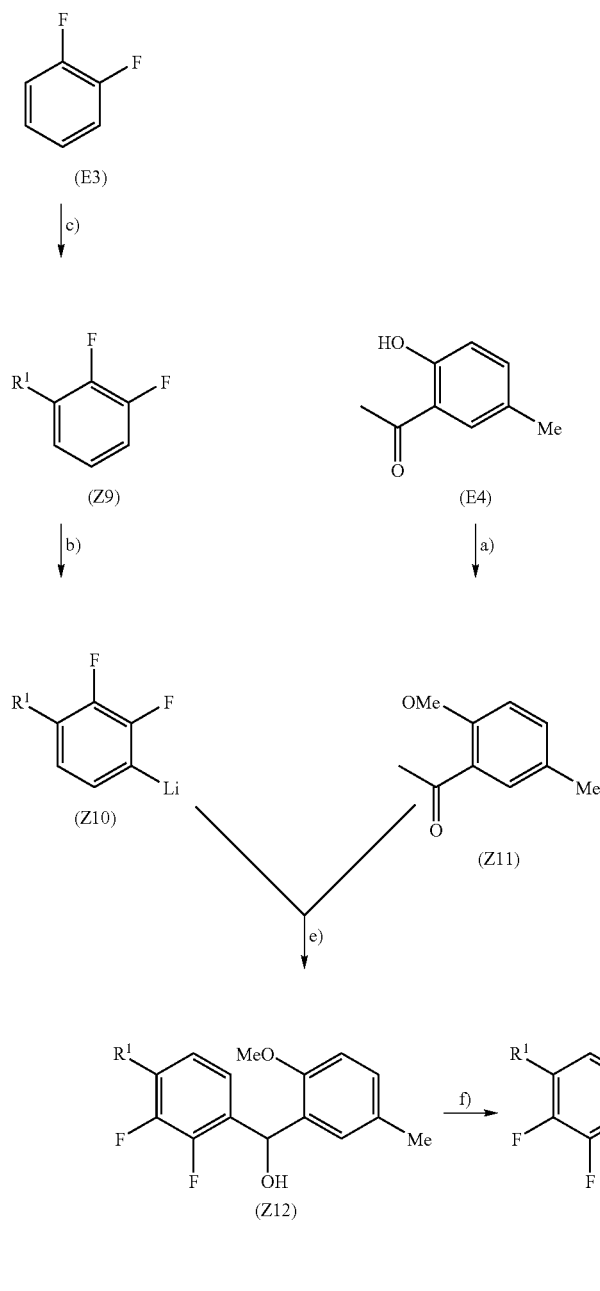

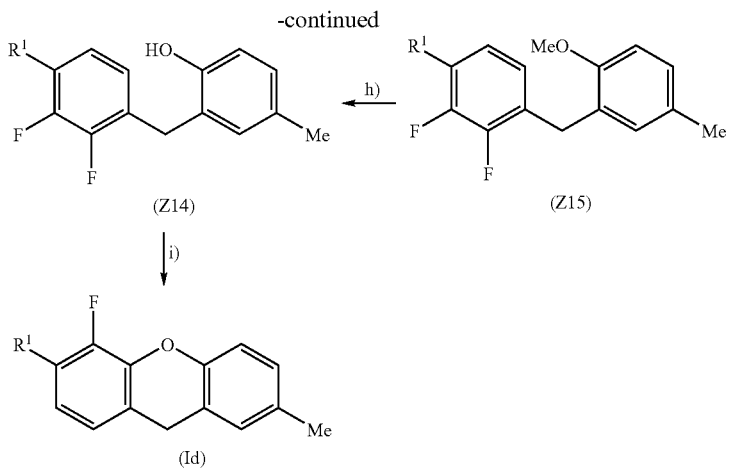

The invention is illustrated in detail by the examples which follow.

EXAMPLE 1

3,4,5-Trifluoro-2-methyl-6-propyl-9H-xanthene
(Formula Ib where $R^1$=propyl and $R^4$=methyl)

Stage a) A solution of 50 mmol of 2,3,4-trifluoro-5-methylbenzaldehyde in 30 ml of tetrahydrofuran [corresponds to (Z4) in Scheme 1] was added dropwise at −75° C. with stirring to a solution of 48 mmol of 1-lithio-2-methoxy-3-fluorobenzene [corresponds to (Z2) in Scheme 1] in 100 ml of tetrahydrofuran. Within 2 hours, the mixture was brought to room temperature with stirring, admixed with saturated NH$_4$Cl solution and extracted twice with 200 ml each time of tert-butyl methyl ether, and the organic phases were combined, washed with saturated NaCl solution and then water, and dried over sodium sulfate. The solvents were distilled off under reduced pressure, and the residue was taken up in dichloromethane and filtered through a suction filter having a 10 cm-thick layer of silica gel.

Stage b) The solution, obtained from step a), of the crude (3-fluoro-2-methoxyphenyl)(2,3,4-trifluoro-5-methylphenyl)methanol [(Z5) in Scheme 1] was admixed at 0° C. with 50 mmol of 4-toluenesulfonyl chloride and 60 mmol of pyridine; after 5 h, the mixture was adjusted to pH 2 by adding semiconcentrated hydrochloric acid, and the organic phase was washed with water and dried over sodium sulfate. After chromatographic purification on silica gel with dichloromethane as the eluent, 31 mmol of [(3-fluoro-2-methoxyphenyl)(2,3,4-trifluoro-5-methylphenyl)methyl]-4-toluenesulfonic ester [(Z6) in Scheme 1] were obtained.

Stage c) A solution of 15 mmol of [(3-fluoro-2-methoxyphenyl)(2,3,4-trifluoro-5-methylphenyl)methyl]-4-toluenesulfonic ester in 15 ml of tetrahydrofuran was added dropwise at 20° C. to a suspension of 40 mmol of lithium aluminum hydride in 40 ml of tetrahydrofuran. To complete the reaction, the mixture was heated to reflux overnight. After customary hydrolytic workup, the mixture was extracted twice with 100 ml each time of tert-butyl methyl ether, the combined organic phases were washed with saturated sodium chloride solution and then water and dried over sodium sulfate, and the solvents were removed under reduced pressure. The residue [2,3,4-trifluoro-1-(3-fluoro-2-methoxybenzyl)-5-methylbenzene; (Z8) in Scheme 1] was used in the subsequent stage without purification.

Stage d) The crude product of stage c) was dissolved in 50 ml of dichloromethane and admixed at −10° C. with a solution of 15 mmol of boron tribromide in 15 ml of dichloromethane. After stirring at room temperature overnight, a pH of 3 was established by adding ice-water and then hydrochloric acid, and the organic phase was removed, washed with saturated NaCl solution and then water, and dried over sodium sulfate. After chromatographic purification using silica gel (1. dichloromethane 2. dichloromethane+20% by volume of ethyl acetate) and distilling off the solvents, 11 mmol of 2-fluoro-6-(2,3,4-trifluoro-5-methylbenzyl)phenol [(Z7) in Scheme 1] were obtained.

Stage e) The product from stage d) was dissolved in 100 ml of dimethylformamide, admixed with 30 mmol of potassium carbonate and heated to 100° C. On completion of reaction (monitoring by means of thin-layer chromatography), the mixture was poured onto 500 ml of ice-water and extracted twice with 100 ml each time of dichloromethane, and the combined organic phases were washed with saturated sodium chloride solution and then water, and dried over sodium sulfate. After chromatographic purification (silica gel, dichloromethane) and distilling off the solvent under reduced pressure, 4.1 mmol of 3,4,5-trifluoro-2-methyl-9H-xanthene [(Ib) where $R^1$=H in Scheme 1] were obtained.

Stage f) 4 mmol of n-butyllithium (1.6 M in hexane) were slowly added dropwise at an internal temperature of ≦−70° C. under a protective gas atmosphere to a solution of 3.5 mmol of the product of the stage e) in 15 ml of tetrahydrofuran, and the mixture was stirred for a further 30 min. At the same temperature, a solution of 4 mmol of potassium tert-butoxide in 10 ml of tetrahydrofuran was subsequently added dropwise. The dark brown solution was cooled to from −90 to −100° C., and 7.5 mmol of 1-bromopropane were metered in at this temperature. The mixture was first stirred at −70° C. for 2 h, then brought to room temperature with stirring overnight. The mixture was then poured onto double the amount of ice-water, pH 4 was established by adding hydrochloric acid, the mixture was extracted twice with 100 ml each time of tert-butyl methyl ether, and the organic phases were combined, washed with saturated sodium chloride solution and then water, and dried over sodium sulfate. The residue obtained after the solvents had been distilled off was purified by chromatography (silica gel, toluene) and by recrystallization from acetonitrile. 2.2 mmol of 3,4,5-trifluoro-2-methyl-6-propyl-9H-xanthene were obtained.

EXAMPLE 2

6-Ethyl-5-fluoro-2-methyl-9H-xanthene (formula Id where $R^1$=ethyl and $R^4$=methyl) was obtained according to example 1 using 4-ethyl-2,3-difluorophenyllithium [(Z10) in Scheme 2] and 2-methoxy-5-methylbenzaldehyde [(Z11 in Schem 2] in stage a).

USE EXAMPLE 1

A chiral-smectic C mixture consisting of

| | |
|---|---|
| 2-(4-Heptyloxyphenyl)-5-nonylpyrimidine | 19.6% |
| 5-Nonyl-2-(4-octyloxyphenyl)pyrimidine | 19.6% |
| 5-Nonyl-2-(4-nonyloxyphenyl)pyrimidine | 19.6% |
| 2-(2,3-Difluoro-4-heptyloxyphenyl)-5-nonylpyrimidine | 6.5% |
| 2-(2,3-Difluoro-4-octyloxyphenyl)-5-nonylpyrimidine | 6.5% |
| 2-(2,3-Difluoro-4-nonyloxyphenyl)-5-nonylpyrimidine | 6.5% |
| 5-Hexyloxy-2-(4-hexyloxyphenyl)pyrimidine | 19.6% |
| (S)-4-[4'-(2-Fluorooctyloxy)biphenyl-4-yl]-1-heptylcyclohexanecarbonitrile | 2.0% | was admixed with 5% of the compound from example 1.

This results in a mixture which, as demonstrated by FIG. 1, is suitable for the operation of displays in inverse mode, since the curved profile has the required minimum and the values are within the technically relevant range.

Figure 1:
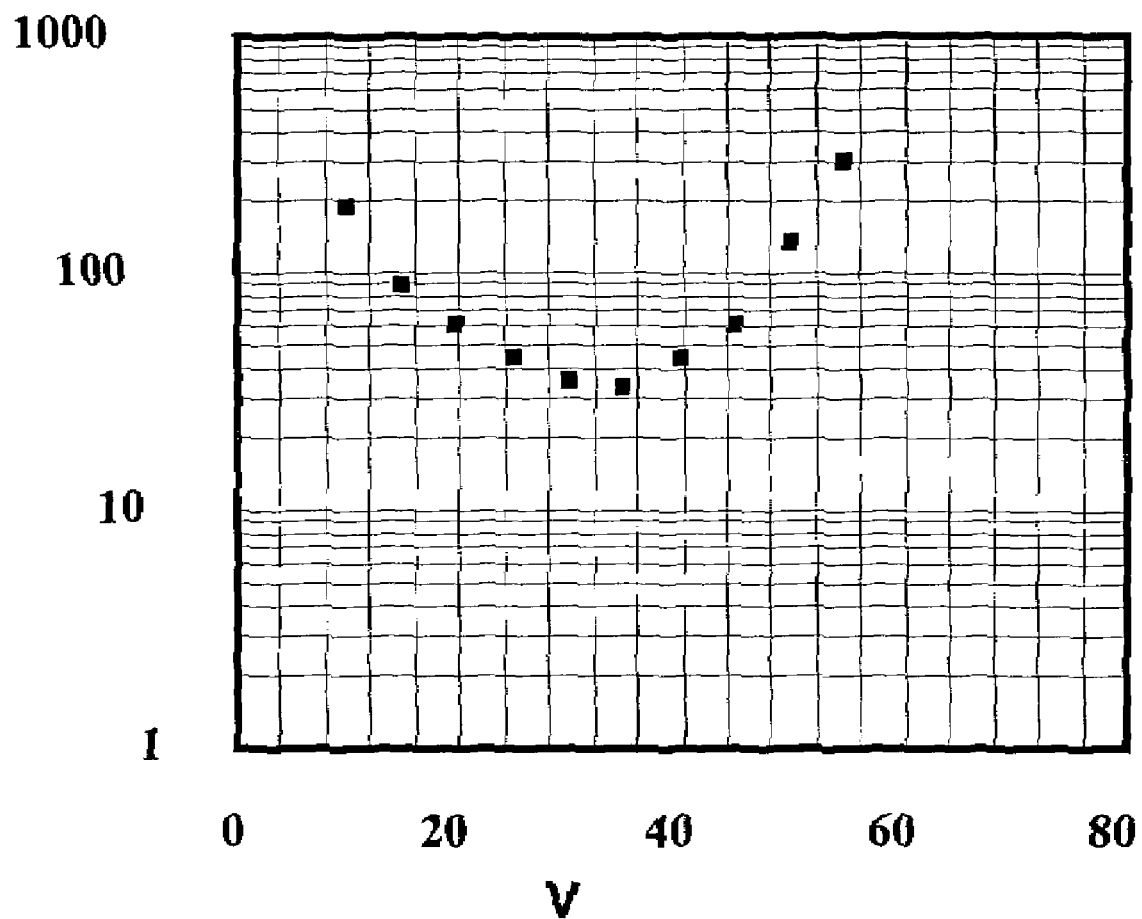
FIG. 1 shows the τVmin curve (τ plotted against the voltage in volts) at $T_C$-30K, monopolar pulses and a cell separation of 1.3 μm.

What is claimed is:

1. A compound of the formula (I)

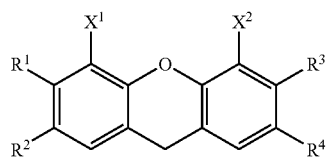

(I)

in which $R^1$, $R^3$ are each independently
a) H
b) one of $R^1$ and $R^3$ is —$M^1$—$A^1$—$R^5$
c) a straight-chain or branched alkyl radical having from 1 to 16 carbon atoms or a straight-chain or branched alkenyl radical having from 2 to 16 carbon atoms, in which
 c1) one or more nonadjacent and nonterminal $CH_2$ groups may be replaced by —O—, —C(=O)O—, —O—C(=O)—, —O—C(=O)—O—, —C(=O)— or —Si(CH_3)_2— and/or
 c2) one $CH_2$ group may be replaced by —C≡C—, cyclopropane-1,2-diyl, cyclobutane-1,3-diyl, cyclohexane-1,4-diyl or phenylene-1,4-diyl and/or
 c3) one or more hydrogen atoms may be replaced by F and/or Cl
d) F, Cl, $CF_3$, $OCF_3$, $OCF_2H$ $R^2$, $R^4$ are each independently
a) H
b) one of $R^2$ and $R^4$ is —$M^1$—$A^1$—$R^5$
c) a straight-chain or branched alkyl radical having from 1 to 16 carbon atoms or a straight-chain or branched alkenyl radical having from 2 to 16 carbon atoms, in which
 c1) one or more nonadjacent and nonterminal $CH_2$ groups may be replaced by —O—, —C(=O)O—, —O—C(=O)—, —O—C(=O)—O—, —C(=O)— or —Si(CH_3)_2— and/or
 c2) one $CH_2$ group may be replaced by —C≡C—, cyclopropane-1,2-diyl, cyclobutane-1,3-diyl, cyclohexane-1,4-diyl or phenylene-1,4-diyl and/or
 c3) one or more hydrogen atoms may be replaced by F and/or Cl $X^1$, $X^2$ are each independently H or F $M^1$ is —CO—O—, —O—CO—, —$CH_2$—O—, —O—$CH_2$—, —$CF_2$—O—, —O—$CF_2$—, —CH=CH—, —CF=CF—, —C≡C—, —$CH_2$—$CH_2$—CO—O—, —O—CO—$CH_2$—$CH_2$—, —$CH_2$—$CH_2$—, —$CF_2$—$CF_2$—, —($CH_2$)_4—, —OC(=O)CF=CF— or a single bond $A^1$ is 1,4-phenylene in which one or two hydrogen atoms may be replaced by F, Cl, CN and/or $OCF_3$ or three hydrogen atoms may be replaced by fluorine, 1,4-cyclohexylene in which one or two hydrogen atoms may be replaced by $CH_3$ and/or F, 1-cyclohexene-1,4-diyl in which one hydrogen atom may be replaced by $CH_3$ or F, or 1,3-dioxane-2,5-diyl and $R^5$ has the same possible definitions as specified for $R^2$ and $R^4$, with the exception of —$M^1$—$A^1$—$R^5$, but independently of the particular definitions of $R^2$ and $R^4$ with the following provisos:
1) at least one of $X^1$, $X^2$ has to be F
2) $R^1$, $R^2$, $R^3$ and $R^4$ must not at the same time be H
3) at most two of $R^1$, $R^2$, $R^3$, and $R^4$ are c).

2. A compound as claimed in claim 1, which corresponds to one of the formulae (Ia) to (Id)

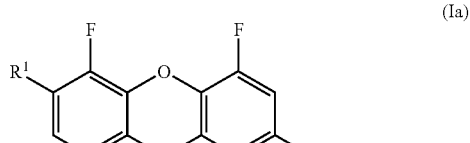

(Ia)

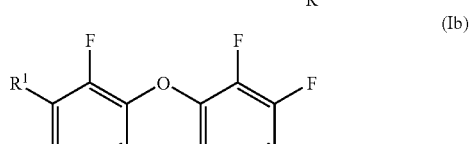

(Ib)

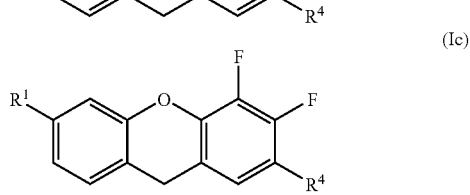

(Ic)

-continued

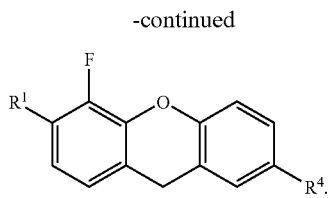

(Id)

3. A compound as claimed in claim 2, in which $R^1$ and $R^4$ in the compounds of the formulae (Ia), (Ib), (Ic) and (Id) are each independently an alkyl or alkyloxy radical having from 1 to 6 carbon atoms or an alkenyl or alkenyloxy radical having from 2 to 5 carbon atoms or the $R^5$—$A^1$—$M^1$- moiety, with the proviso that $R^1$ and $R^4$ must not at the same time be $R^5$—$A^1$—$M^1$—.

4. A liquid-crystal mixture which comprises one or more compounds of the formula (I) as claimed in claim 1.

5. The liquid-crystal mixture as claimed in claim 4, which comprises one or more compounds of the formula (I) in an amount of from 1 to 40% by weight, based on the liquid-crystal mixture.

6. The liquid-crystal mixture as claimed in claim 4, wherein the mixture comprises at least three further components having smectic and/or nematic and/or cholesteric phases.

7. The liquid-crystal mixture as claimed in claim 4, which is chiral-smectic.

8. The liquid-crystal mixture as claimed in claim 4, which is nematic or cholesteric.

9. A liquid-crystal display comprising the liquid-crystal mixture as claimed in claim 4.

10. The liquid-crystal display as claimed in claim 9, wherein the display is operated in ECB, IPS or VA display mode and comprises the liquid-crystal mixture which is nematic or cholesteric.

11. The compound as claimed in claim 3, in which $R^1$ and $R^4$ in the compounds of the formulae (Ia), (Ib), (Ic) and (Id) are each independently an alkyl or alkyloxy radical having from 1 to 6 carbon atoms or an alkenyl or alkenyloxy radical having from 2 to 5 carbon atoms.

12. The compound as claimed in claim 3, in which $R^1$ and $R^4$ in the compounds of the formulae (Ia), (Ib), (Ic) and (Id) are each independently methyl, ethyl or propyl.

13. The compound as claimed in claim 3, in which $R^1$ is methyl, ethyl or propyl and $R^4$ is methyl in the compounds of the formulae (Ib) and (Id).

14. A liquid-crystal mixture which comprises one or more compounds of the formula (I) as claimed in claim 11.

15. A liquid-crystal mixture which comprises one or more compounds of the formula (I) as claimed in claim 12.

16. A liquid-crystal mixture which comprises one or more compounds of the formula (I) as claimed in claim 13.

17. A liquid-crystal display comprising the liquid-crystal mixture as claimed in claim 14.

18. A liquid-crystal display comprising the liquid-crystal mixture as claimed in claim 15.

19. A liquid-crystal display comprising the liquid-crystal mixture as claimed in claim 16.

* * * * *